United States Patent [19]

Gory et al.

[11] Patent Number: 5,300,086
[45] Date of Patent: Apr. 5, 1994

[54] DEVICE WITH A LOCATING MEMBER FOR REMOVABLY IMPLANTING A BLOOD FILTER IN A VEIN OF THE HUMAN BODY

[76] Inventors: Pierre Gory, 02, Boulevard Clemenceau; Gilles Bovyn, 03, rue Monseigneur Morelle, both of, 22000 Saint-Brieuc, France

[21] Appl. No.: 985,178
[22] Filed: Dec. 2, 1992

Related U.S. Application Data

[63] Continuation-in-part of Ser. No. 731,536, Jul. 17, 1991, abandoned.

[51] Int. Cl.$^5$ ............................................. A61M 29/00
[52] U.S. Cl. .................................... 606/200; 128/899; 604/175
[58] Field of Search ................ 128/899; 604/104–106, 604/164–165, 171, 175, 280; 606/191, 194, 198, 200

[56] References Cited

U.S. PATENT DOCUMENTS

| | | | |
|---|---|---|---|
| 4,553,961 | 11/1985 | Pohndorf et al. | 604/175 |
| 4,832,055 | 5/1989 | Palestrant | 128/899 |
| 4,834,713 | 5/1989 | Suthanthiran | 604/175 |
| 4,969,891 | 11/1990 | Gewertz | 606/200 |
| 5,152,777 | 10/1992 | Goldberg et al. | 606/200 |

*Primary Examiner*—C. Fred Rosenbaum
*Assistant Examiner*—Corrine Maglione
*Attorney, Agent, or Firm*—Thomas R. Morrison

[57] ABSTRACT

This device comprises an elastic guide wire onto which is fitted a semi-rigid tubular mandrel which is in turn fitted into a thin-walled tubular sheath. A catheter in the form of an easily divisible flexible tube has a distal end that permanently holds a blood filter. The catheter's proximal end receives a locating member that can be confined under the skin of a patient to insure that no infection develops. After the filter is temporarily implanted, a removable strengthening cable can be inserted into the catheter to advance the filter along the sheath to a chosen position in a vein, in particular the inferior vena cava, of the patient. The locating member makes it easy to remove the filter whenever the risk of pulmonary embolism is no longer present.

5 Claims, 3 Drawing Sheets

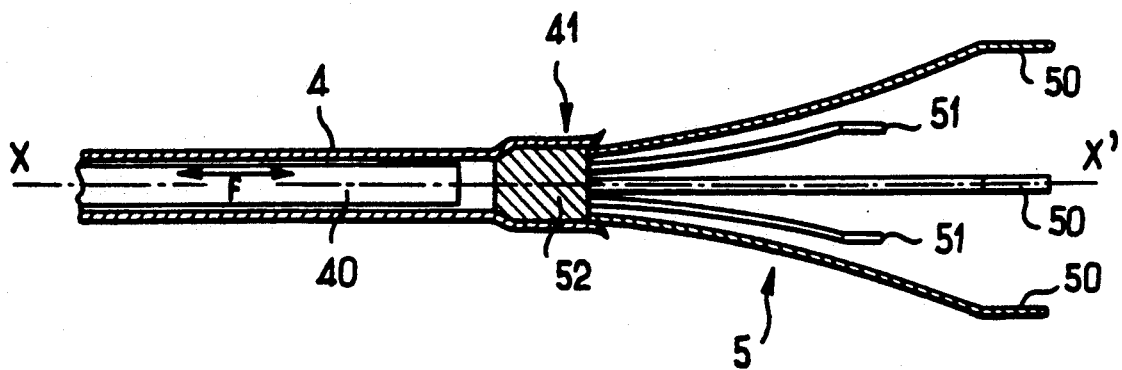
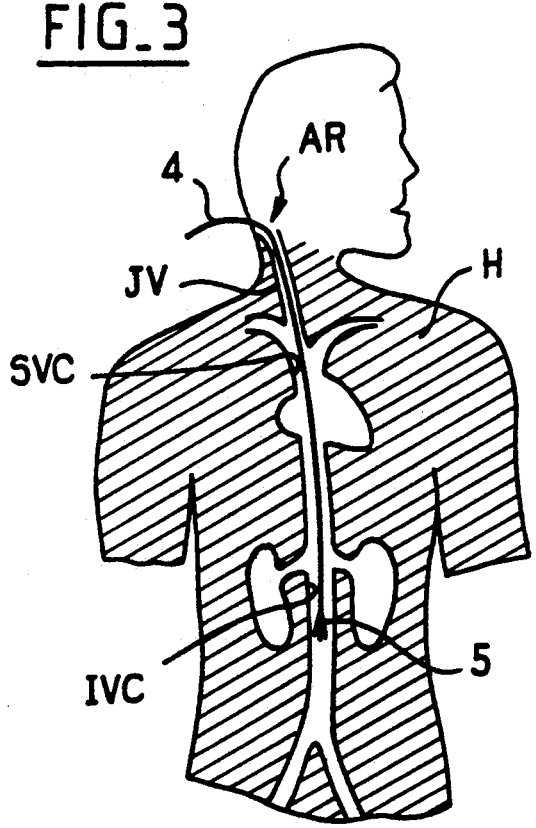
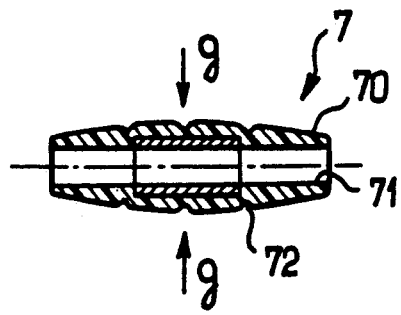
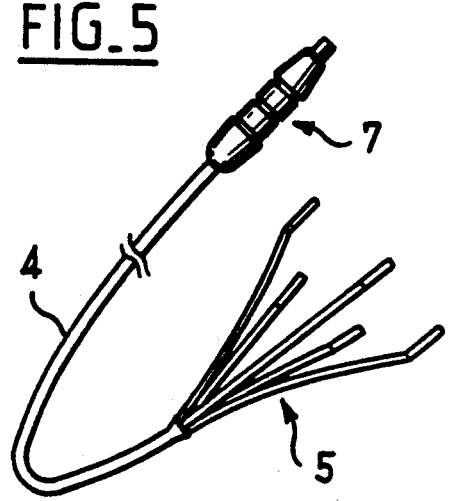

DEVICE WITH A LOCATING MEMBER FOR REMOVABLY IMPLANTING A BLOOD FILTER IN A VEIN OF THE HUMAN BODY

This application is a continuation-in-part of pending application Ser. No. 07/731,536 filed Jul. 17, 1991, now abandoned.

BACKGROUND OF THE INVENTION

This invention relates to a device for temporarily implanting, in a vein of the human body, and in particular in the inferior vena cava of a patient, a blood filter, and more particularly a blood filter of the type that is elastically expandable in the radial direction.

The function of blood filters is to hold back the blood clots that may form in the course of phlebitis or other vascular or cardiovascular disorders, in order to prevent their migration towards the pulmonary arteries where they could cause an embolism.

The filters generally used for this purpose have the shape of a small umbrella consisting of a plurality of flexible branches that can be radially expanded. In the rest position (retracted state) the branches extend approximately parallel to one another and occupy a reduced dimension in the radial direction, and this allows them to be positioned in a vein. Once in place inside the vein, the branches spread automatically outward and are immobilized against the wall of the vein, thereby anchoring the filter at the desired site.

Filters of this type are preferably positioned in the inferior vena cava, a little below the level of the kidneys.

The equipment that permits positioning of the filter traditionally comprises a guide rod and a mandrel which make it possible to insert a sheath into the vein to the desired depth, in such a way that the end of the sheath arrives at the site where the filter is to be positioned. When the filter is positioned in the inferior vena cava, it is known to carry out the implanting via a percutaneous access route or by "denudation" at the level of the right internal jugular vein. The positioning is thus carried out starting from the jugular vein, and via the superior vena cava. After the sheath is positioned, the mandrel and the guide rod are withdrawn. The filter is then introduced into the sheath by a special syringe and displaced inside the sheath, along its entire length, by the mandrel, the latter in this case having the role of a pusher. When the filter arrives at the free end of the sheath (previously positioned at the desired site in the inferior vena cava), the filter spreads open automatically and anchors in the wall of the vein. The sheath is then removed, and the filter remains permanently in position.

The main disadvantage of this technique is that the filter can be withdrawn only by performing a very delicate surgical operation. Unfortunately, the permanent positioning of the filter in the vena cava is a source of complications, in particular, the filter can trigger a thrombosis. Moreover, the patient with this filter in place must take anticoagulant medication for life.

These disadvantages are all the more regrettable since, in a great many forms of treatment, the positioning of the filter in the vein is necessary only for a limited period, generally a few weeks or a few months, corresponding to the period during which there is a real risk of embolism.

For this reason a technique has recently been proposed for implanting the filter temporarily and removably, so it can be withdrawn after a certain time has elapsed.

For this, the mandrel which is used for implanting the filter is permanently integral with the latter; after the filter is implanted, the mandrel remains inserted in the vein and projects from the body via the access route used for the implanting, that is, at the level of the neck, in the region of the jugular vein, when the filter is implanted in the vena cava. Unfortunately, such a rod, which is relatively rigid, is very uncomfortable for the patient; moreover, because the mandrel projects from the skin, it constitutes a source of infection that may lead to serious complications, especially septicaemia.

OBJECTS AND SUMMARY OF THE INVENTION

An object of the present invention is to overcome the disadvantages of the prior art by a new device for implanting a blood filter of the type mentioned above, this device being simple to manipulate, use, and implant reversibly, without the patient being exposed to real risks of infection or traumatized by the presence of the implanted device throughout the period during which the filter must remain in place.

In the description and claims that follow, the terms "proximal" and "distal" are used with reference to the point on the body of the patient through which the blood filter is introduced. According to this definition, the proximal end of an element is that which is nearest the point of introduction, and the distal end is that which is furthest away from that point.

The device of the present invention is provided with a locating member adapted to be disposed subcutaneously for localizing, through the skin of the patient, the catheter to whose distal end the filter is fixed. Especially to avoid infection, the locating member will comprise a sleeve of a biocompatible material that encloses an internal closing means at the catheter's proximal end. The internal closing means can close off the catheter.

Further, the apparatus of the present invention will advantageously be composed of the following elements:

a) an elastic guide wire of small diameter intended to be inserted into the vein via a percutaneous access route or after denudation;

b) a semi-rigid tubular mandrel capable of being fitted onto the guide wire and displaced along the latter;

c) a thin-walled tubular sheath capable of being fitted onto the mandrel and positioned inside the vein by displacing the mandrel along the guide wire;

d) the catheter having the form of an easily divisible flexible tube whose distal end permanently holds the blood filter;

e) a strengthening cable capable of being removably inserted into the catheter, thereby making it possible to advance, inside the previously positioned sheath, the catheter and its filter in the retracted state, until the latter emerges at the distal end of the sheath and spreads open automatically to anchor against the wall of the vein;

f) the locating member, which is thus intended to be fixed at the proximal end of the catheter after removing the strengthening cable and cutting the catheter at the level of the access route.

Furthermore, according to a certain number of advantageous but not restrictive characteristics:

the proximal ends of the mandrel and of the sheath each bear a head in the form of a female sleeve that meets LUER international standards. The head borne by the mandrel is adapted to butt against the head borne by the sheath, in order to facilitate their point positioning inside the vein;

the device comprises a tubular syringe body, fitted onto the catheter, that receives the blood filter and holds the latter in the retracted state;

the proximal end of the head borne by the sheath and the distal end of the syringe body are provided with complementary coupling means that satisfies the so-called "LUER-Lock" standards, such as a threading-/tapping, thereby facilitating the introduction of the filter into the previously positioned sheath;

the locating member has the form of a sleeve intended to be crimped onto the catheter;

the locating member is a sleeve free from sharp angles; for example, it may be ovoid in shape;

the locating member is made of plastic material cast on a deformable metal ring;

if the deformable metal ring is closely crimped onto the catheter, it can constitute the above-mentioned catheter proximal-end closing means. Otherwise, a plug inserted into the catheter end through the central opening of the sleeve can be used as such a closing means;

the catheter is made of plastic material, for example, polyvinyl chloride covered with a biocompatible material such as a silicone-based material;

the distal end of the mandrel bears a radiopaque marker, for example, a metal ring;

the distal end of the catheter, which bears the filter, is also closed. In many cases this feature could be important, since it prevents blood flowing back into the catheter towards the latter's proximal end. Further, if the catheter is thus closed at both its distal and its proximal ends, the risk of infection will be further limited.

Briefly stated, the present invention provides
According to an embodiment of the invention,
According to a feature of the invention,
The above, and other objects, features and advantages of the present invention will become apparent from the following description read in conjunction with the accompanying drawings, in which like reference numerals designated the same elements.

BRIEF DESCRIPTION OF THE DRAWINGS

FIG. 2 shows in longitudinal cross-section the distal end of the catheter fitted with the blood filter.

FIG. 3 is a diagrammatic view illustrating the positioning of the filter in the inferior vena cava of a patient.

FIG. 4 is a longitudinal cross-sectional view of a first embodiment of the locating member.

FIG. 5 is a diagrammatic view of the catheter whose proximal and distal ends are provided, respectively, with the embodiment of the locating member shown in FIG. 4 and with the filter.

DETAILED DESCRIPTION OF THE PREFERRED EMBODIMENTS

Figure 1:
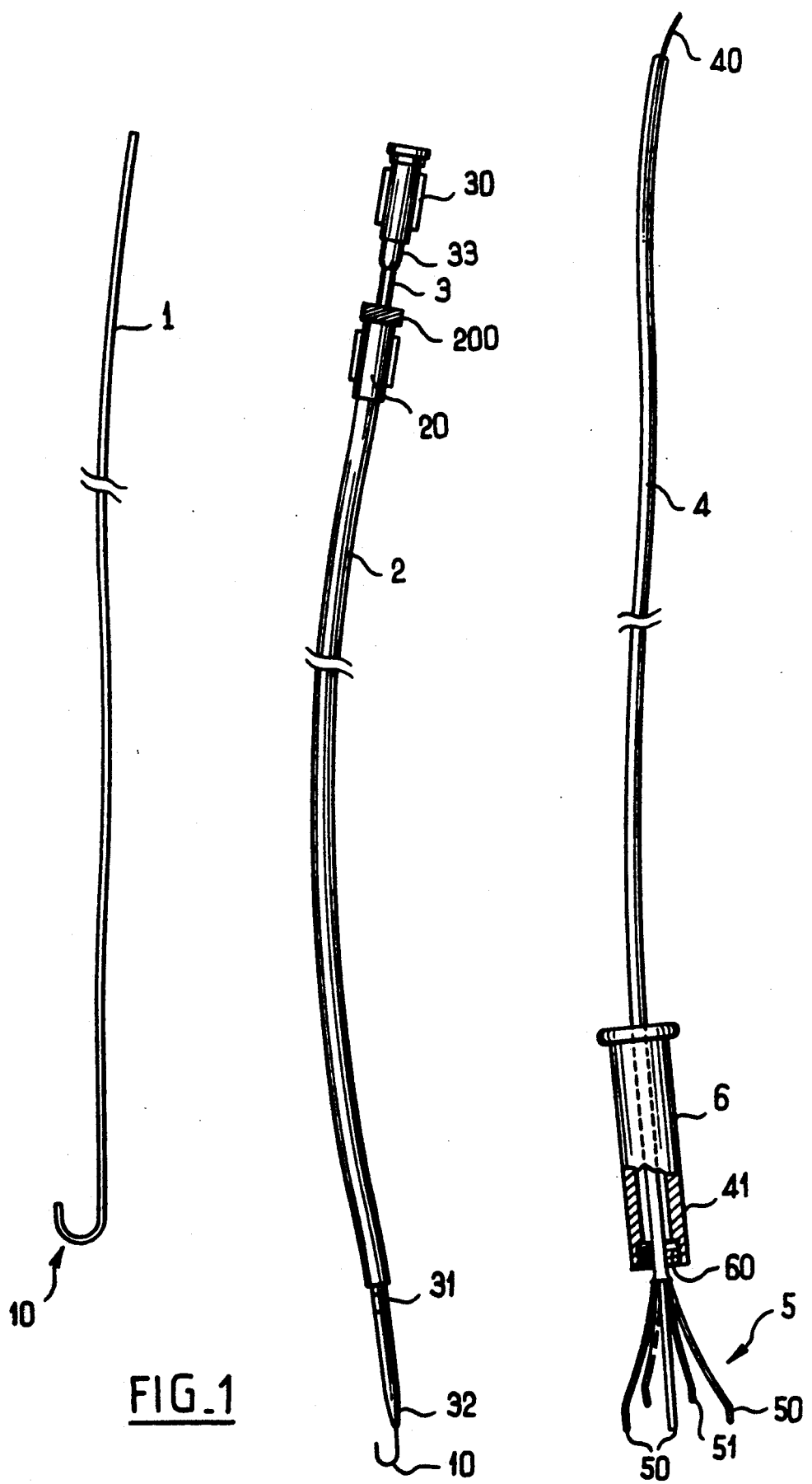
FIG. 1 shows the various elements constituting the device.

The various main elements constituting the device and shown in the drawings have been given reference numbers as follows: a guide wire 1, a tubular sheath 2, a tubular mandrel 3, a catheter 4, a filter 5, a strengthening cable 40, a locating member 7, and a syringe body 6.

Referring to FIG. 1, wire 1 of small diameter, made, for example, of metal, which, though elastically flexible, possesses a certain rigidity. Wire 1 has a distal end 10 that is curved to form a half loop, which gives wire 1 the general appearance of the letter J.

Sheath 2 is a thin-walled, cylindrical tube made of plastic material, for example, polyvinyl chloride. It is open at its two ends. At its proximal end, it holds a sleeve-shaped head 20, likewise of plastic material, whose diameter is greater than the external diameter of sheath 2. Sheath 2 has a certain flexibility. On the free end (proximal side) of head 20 is a threading 200 consisting of one or more threads (LUER-Lock standards).

Tubular mandrel 3 consists of a rod made of semi-rigid plastic material whose internal diameter corresponds to the diameter of wire 1, thereby allowing mandrel 3 to be fitted onto wire 1. Mandrel 3's external diameter corresponds to the internal diameter of sheath 2, thereby allowing sheath 2 to be fitted onto mandrel 3.

The fitting of mandrel 3 onto wire 1 and of sheath 2 onto the mandrel leaves sufficient play to permit relative longitudinal sliding of these three elements.

Tubular mandrel 3 holds at its proximal end a sleeve-shaped head 30 of LUER standards. Head 30 has a cylindrical or slightly conical extension 33 which is adapted to be engaged in a complementary seat provided in sheath head 20. After engagement of their respective heads, sheath 2 and mandrel 3 are perfectly integral with one another to such an extent that, by manipulating only one of the two heads 20, 30, it is possible to displace the entire assembly of mandrel 3 and sheath 2. Mandrel 3 has a distal end 32 of a smooth, conical shape with a rounded tip, whereby it avoids causing trauma during implanting of the device.

At a short distance from end 32, mandrel 3 is provided with a radiopaque marker 31, consisting, for example, of a small metal ring. The relative lengths of sheath 2 and of mandrel 3 are determined so that, after complete insertion of mandrel 3 into the sheath 2 (with head 30 in abutment against head 20), marker 31 just emerges at the distal end of sheath 2.

Catheter 4 consists of a very flexible (nonrigid) tube whose external diameter is substantially smaller than that of sheath 2. Catheter 4 is made of a plastic material covered with a biocompatible material such as a silicone based material; the plastic material is, for example, polyvinyl chloride. Mandrel 3 is advantageously made radiopaque, for example by including particles of barium sulfate in the material of which it is made.

As already mentioned, catheter 4 has a tubular shape, and it can receive in its central lumen a strengthening cable 40 of corresponding diameter, this cable consisting, for example, of a very thin wire of spring steel wound spirally about itself over its entire length.

Referring to FIG. 2, the distal end of catheter 4 is closed by a closure plug 52 which forms part of filter 5. The sliding of strengthening cable 40 within catheter 4 (indicated by a double arrow f in FIG. 2) is thus limited in the distal direction, so that cable 40 serves as a pusher upon introduction of catheter 4, as will be explained below.

Filter 5 is a filter of a known type, of the kind described in the Background section above. In the embodiment illustrated, filter 5 has the form of an umbrella frame which comprises eight branches consisting of thin, flexible, metal strips. There are four long branches 50 alternating with four short branches 51 in a uniform angular distribution of 45°.

Branches 50, 51 are embedded at their proximal ends in closure plug 52 of catheter 4. The distal ends of branches 50, 51 are slightly curved to present a direction essentially parallel to the longitudinal axis XX' both of filter 5 and of catheter 4. It will thus be understood that, when filter 5 is in the unfurled state (as illustrated in the figures), the free ends of branches 50, 51 come to lie correctly against the wall of the vein without risk of trauma to the latter.

Referring again to FIG. 1, the device of the present invention also comprises syringe body 6 of plastic material, which has the shape of a tubular sleeve able to slide on catheter 4. The length of body 6 is slightly greater than the length of branches 50, 51 of filter 5. The internal diameter of body 6 corresponds essentially to the internal diameter of sheath head 20 and of sheath 2.

The distal end of body 6 is tapped so as to present a threading 60 complementary with threading 200 of sheath head 20 in accordance with the LUER standards.

Referring to FIGS. 4 and 5, locating member 7 comprises a body 70 in the shape of a small sleeve made of flexible plastic material. This sleeve, free of sharp angles, has the general shape of a small olive whose more bulging central part is cast on a metal ring 72.

As is illustrated in FIG. 4 by the arrows g, crimping locating member 7 onto a rod previously fitted into a central hole 71 of body 70, and consequently the fixing of locating member 7 on this rod, can be easily done by crushing the central zone of body 70 and consequently deforming ring 72. As will be seen below, it is thus possible to fix locating member 7 at the proximal end of catheter 4 in a simple manner.

We will now explain how the device which has just been described positions a blood filter in the inferior vena cava of a human body in a reversible manner, it being possible for the filter to be easily removed later.

The filter is implanted under local anesthesia into a human body, designated H in FIG. 3. In the conventional manner, the surgeon begins by forming in the neck a percutaneous access route AR in the right internal jugular vein JV, or by carrying out denudation.

In a first stage, the surgeon introduces guide wire 1 into the jugular vein. With radiological monitoring, made possible by the radiopacity of wire 1, the surgeon lowers wire 1 through the jugular vein and to follow the superior vena cava SVC and then the inferior vena cava IVC. Because distal end 10 of guide wire 1 is curved, there is no hitching or trauma during its travel. This operation finishes when distal end 10 has arrived slightly beyond the zone where filter 5 is to be implanted, generally below the bifurcations of renal irrigation.

The surgeon then makes a small incision for widening on both sides of the entry point of guide wire 1, in order to facilitate the operation that follows.

In a second stage, head 30 being in abutment against head 20, the surgeon fits onto the proximal end of guide wire 1 (which of course projects from the jugular vein) the single assembly consisting of mandrel 3 and sheath 2. The surgeon lowers this assembly gently along guide wire 1 until radiopaque marker 31 reaches the zone intended for anchoring filter 5.

In a third stage, the surgeon withdraws guide wire 1 and mandrel 3 from sheath 2.

In a fourth stage, while syringe body 6 covers filter 5, which is consequently in the folded-in state, the surgeon connects syringe body 6 onto head 20 of the sheath 2 with the aid of complementary threadings 60, 200.

In a fifth stage, with strengthening cable 40 situated inside catheter 4, the surgeon lowers the catheter 4/cable 40 assembly so that filter 5, still in the retracted state, is transferred first into head 20 and then into sheath 2. The pushing force applied by the surgeon on the distal end of the catheter 4/cable 40 assembly is transmitted correctly to filter 5 on account of the strengthening role of cable 40, so that filter 5 descends progressively along the sheath 2. This progressive descent would be difficult in the absence of cable 40 on account of the flexibility of catheter 4 (which is semi-rigid).

When filter 5 has arrived at the distal end of sheath 2, it spreads open automatically as a result of the flexibility of branches 50, 51, which come to bear against the walls of the vena cava at the desired site. This accomplishes the anchoring of filter 5.

In a sixth stage, the surgeon withdraws sheath 2 from the vein.

In a seventh stage, the surgeon withdraws cable 40 from catheter 4 and then cuts catheter 4 outside the jugular vein, at a short distance from the latter. This cutting can be carried out conveniently, for example, using a pair of ordinary surgical scissors, because catheter 4 is easily divisible.

In an eighth stage, the surgeon fits locating member 7 onto the protruding proximal end of catheter 4, then fixes locating member 7 by crimping with the aid of a suitable tool, for example, a pincer.

Finally, the surgeon forms, via the small widening incision, a small space under the platysma of the neck, where he tucks in locating member 7. The surgeon then closes the access route AR in a conventional manner, in such a way that locating member 7 remains confined under the skin after suturing. There is therefore no risk of infection by the transcutaneous route at the level of the neck.

It should also be noted that the fact that catheter 4 is closed at its distal end prevents any risk of blood flowing back into catheter 4 in the direction of the access route. In addition, the crimping of locating member 7 onto catheter 4 also seals the latter at its proximal end.

On account of its flexibility, catheter 4 does not in any way inconvenience the patient nor interfere with the patient's activities. It is completely "forgotten" by the patient throughout the period during which the filter must be kept in position in the inferior vena cava. The duration of retention of catheter 4 and of filter 5 can range from a few weeks to several months by virtue of the present invention, in contrast to the only two to three weeks in the prior techniques of temporary positioning, which posed substantial risk of infection.

It is possible at any given time to check the position of locating member 7, either by palpating the skin of the patient or by X-ray. When filter 5 is to be removed, it suffices to reopen the access route AR and to remove filter 5 from the vein by pulling on the end of catheter 4. The special shape of the filter, which can contract freely inward, permits its displacement along the veins IVC, SVC and JV.

The possible principal dimensions of the device are given below purely by way of indication.

Mandrel 3 and sheath 2 can have a length of the order of 50 to 65 cm; catheter 4, a length of the order of 60 to 80 cm; guide wire 1 and cable 40, lengths of the order of 80 to 100 cm.

Guide wire 1 and strengthening cable 40 can have a diameter of the order of 0.5 to 0.7 mm; mandrel 3 and sheath 2 can have external diameters of the order of 3.5 and 4.2 mm, respectively, while catheter 4 can have an external diameter of the order of 2 mm. Long branches 50 of filter 5 can have a length of the order of 40 mm, while short branches 51 can have a length of the order of 25 mm.

After the device is positioned, the effective length of catheter 4, that is, the length between filter 5 and locating member 7, will generally be between 40 and 55 cm.

All the elements constituting the device which is the subject of the invention are intended to be packaged in one and the same sterile packaging, for single use, with a view to their sale and delivery to medical/surgical treatment centers.

It should be clear that other embodiments of a locating member than those illustrated in FIGS. 4 and 5 could be used in the present invention.

Figure 6:
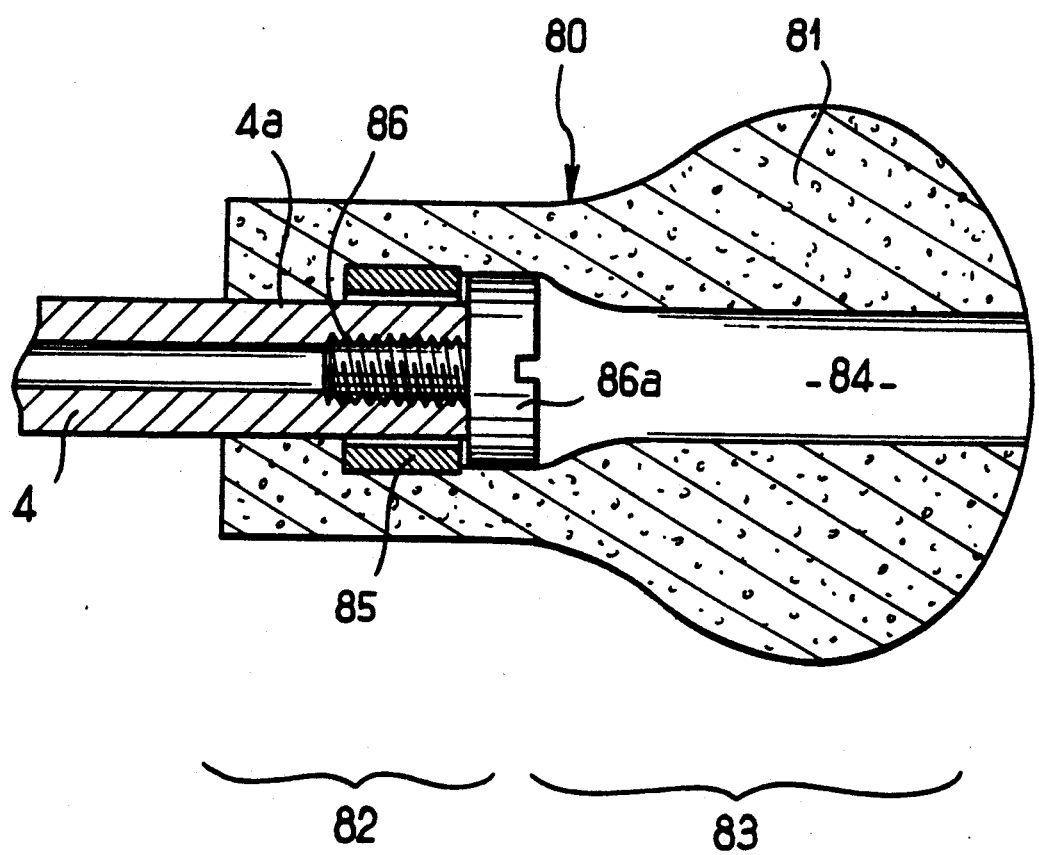
FIG. 6 is a longitudinal cross-sectional view of the proximal end of the catheter to which is fixed a second embodiment of the locating member.

Referring to FIG. 6, one alternative embodiment has a locating member 80 that comprises a sleeve 81 made of a soft plastic material (such as silicone) and having a generally rounded external shape with a cylindrical front portion 82 that has a circular cross-section. Front portion 82 is linked to a substantially spherical or ovoid rear portion 83.

The two portions of sleeve 81 are coaxially crossed through by a central aperture 84 wherein is engaged a proximal end 4a of catheter 4. Proximal end 4a is engaged in aperture 84 within front portion 82 to penetrate through a ring 85 enclosed in sleeve 81 coaxially with aperture 84. Ring 85 is deformable, and can be made of metal, so that it can be crimped or clamped with sleeve 81 on proximal end 4a. In this embodiment, proximal end 4a is closed by a plug 86 engaged therein. Plug 86 can consist of a screw (or its equivalent, such as a notched plug) having an enlarged head 86a extending into aperture 84 and operable therethrough by an appropriate screwdriver. Of course, locating member 80 will be disposed around catheter 4 after division thereof, as previously described.

Having described preferred embodiments of the invention with reference to the accompanying drawings, it is to be understood that the invention is not limited to those precise embodiments, and that various changes and modifications may be effected therein by one skilled in the art without departing from the scope or spirit of the invention as defined in the appended claims.

What is claimed is:

1. Apparatus to be removably implanted in a human body for filtering blood, which comprises;
    a filter adapted for filtering blood in a blood vessel;
    a divisible catheter adapted for implanting in said human body;
    said catheter having a proximal and a distal end;
    said filter being permanently fixed to said distal end of said catheter;
    a locating member adapted to be disposed subcutaneously for localizing said catheter through a skin surface of said human body after said catheter is implanted;
    said locating member being fixed to said proximal end of said catheter;
    said locating member comprising a sleeve enclosing an internal closing means;
    said internal closing means being disposed at said proximal end of said catheter for closing thereof;
    said sleeve having a central opening therethrough; and said internal closing means comprising a plug engaged within said proximal end of said catheter through said central opening.

2. Apparatus as in claim 1, wherein said plug is a screw operable from the exterior of said sleeve through said central opening.

3. Apparatus as in claim 1, wherein said sleeve comprises an internal deformable ring fixed to said proximal end of said catheter; and
    said internal deformable ring is crimped around said proximal end of said catheter wherein said plug is engaged.

4. Apparatus as in claim 1, wherein said filter comprises a plurality of elastically expandable branches having proximal ends;
    said proximal ends of said elastically expandable branches being fixed to a plug means; and
    said plug means being adapted to permanently close said distal end of said catheter.

5. Apparatus to be removably implanted in a human body for filtering blood, which comprises;
    a filter adapted for filtering blood in a blood vessel;
    a divisible catheter adapted for implanting in said human body up to said blood vessel;
    said catheter having a proximal and a distal end;
    said filter being permanently fixed to said distal end of said catheter which is closed by a plug means;
    a locating member adapted to be disposed subcutaneously for localizing said catheter through a skin surface of said human body after said catheter is implanted;
    said locating member being fixed to said proximal end of said catheter;
    said locating member comprising a sleeve having a central opening therethrough wherein said proximal end of said catheter is closely engaged for fixing said sleeve thereto; said sleeve enclosing an internal closing means disposed at said proximal end of said catheter for closing thereof; and
    said internal closing means comprising a screw engaged within said proximal end of said catheter through said central opening of said sleeve.

* * * * *